(12) United States Patent
Nagashima

(10) Patent No.: US 6,515,179 B2
(45) Date of Patent: Feb. 4, 2003

(54) PROCESS FOR THE REMOVAL OF NITROBENZENESULFONYL

(75) Inventor: Nobuo Nagashima, Hyogo (JP)

(73) Assignee: Kaneka Corporation, Osaka (JP)

( * ) Notice: Subject to any disclaimer, the term of this patent is extended or adjusted under 35 U.S.C. 154(b) by 0 days.

(21) Appl. No.: 10/148,877

(22) PCT Filed: Sep. 13, 2001

(86) PCT No.: PCT/JP01/07960

§ 371 (c)(1),
(2), (4) Date: Jun. 11, 2002

(87) PCT Pub. No.: WO02/22549

PCT Pub. Date: Mar. 21, 2002

(65) Prior Publication Data

US 2003/0009056 A1 Jan. 9, 2003

(30) Foreign Application Priority Data

Sep. 14, 2000  (JP) ........................................ 2000-280405

(51) Int. Cl.[7] ..................... C07D 207/16; C07C 271/22; C07C 229/30; C07C 211/27; C07C 215/28
(52) U.S. Cl. ........................ 564/315; 548/533; 548/535; 548/953; 560/157; 560/160; 562/574; 564/355
(58) Field of Search ................................ 564/315, 355; 548/953, 533, 535; 560/157, 160; 562/574

(56) References Cited

FOREIGN PATENT DOCUMENTS

JP  11-171860  6/1999

OTHER PUBLICATIONS

Q. Meng et al.; J. Am. Chem. Soc., (1997) vol. 119, No. 6, pp. 1224–1229. See PCT search report.

Diego A. Alonso et al.; J. Org. Chem., (1998), vol. 63, No. 25, pp. 9455–9461 See PCT search report.

T. Greene et al.; Protective Groups in Organic Synthesis, Third Edition, (1999); pp. 609–610. See PCT search report.

T. Greene et al.; Protective Groups in Organic Synthesis, Third Edition, (1999); pp. 518–520, See PCT search report.

Nippon Kagakukai, "Dai 4 han, Jikken Kagaku Kouza 20; Yuki Gousei II–Alcohol, Amine", Tokyo, Maruzen, Jul. 6, 1992, p. 357. See PCT search report.

Nippon Kagakukai, "Dai 4 han, Jikken Kagaku Kouza 22; Yuki Gousei IV; San, Amino acid, Peptide", Tokyo, Maruzen, Nov. 30, 1992, pp. 144–151. See PCT search report.

*Primary Examiner*—Peter O'Sullivan
(74) *Attorney, Agent, or Firm*—Armstrong, Westerman & Hattori, LLP

(57) ABSTRACT

A 2- or 4-nitrobenzenesulfonamide is allowed to react with an alkali metal alkoxide to remove a nitrobenzenesulfonyl group to thereby obtain an amine corresponding to the amide. Furthermore, a method for producing an amine derivative by allowing the resulting amine without isolation to react with an activated, substituted oxycarbonyl compound or an activated acyl compound is provided. According to this method, a corresponding free amine and its substituted derivative can be produced easily and industrially advantageously from the 2- or 4-nitrobenzenesulfonamide without using a thiol compound.

6 Claims, No Drawings

PROCESS FOR THE REMOVAL OF NITROBENZENESULFONYL

This application is a 371 of Pct/JP01/07960 filed Sep. 13, 2001.

TECHNICAL FIELD

The present invention relates to an improved chemical method for converting a 2- or 4-nitrobenzenesulfonamide to a corresponding amine. The nitrobenzenesulfonamide is a compound in which an amino group is protected with a nitrobenzenesulfonyl group which is a protective group, and is widely used. The method of the present invention is extremely useful as a method for removing the above protective group in producing an optically active amine useful as an intermediate of a pharmaceutical or an agricultural chemical, or an intermediate of a physiologically active substance or the like.

BACKGROUND ART

It is known that a 2- or 4-nitrobenzenesulfonyl group is useful as an amino protective group for an optically active amine or an amino acid which is important as an intermediate of a pharmaceutical or a physiologically active substance, and the group is often used in the course of synthesis of such a compound. As methods for removing the nitrobenzenesulfonyl group, only methods as described below are known in which a thiolate ion is allowed to act in the coexistence of a base:

(1) A method using potassium carbonate as a base, thiophenol as a thiol, and N,N-dimethylformamide as a solvent, which is the most general method (*Tetrahedron Lett.*, 36: 6373 (1995); *J. Am. Chem. Soc.*, 121: 6761 (1999); *Angew. Chem. Int. Ed.*, 39: 1323 (2000); *J. Am. Chem. Soc.*, 122: 976 (2000); and the like);

(2) A method using potassium carbonate as a base, thiophenol as a thiol, and acetonitrile as a solvent (*Tetrahedron Lett.*, 38: 5253 (1997));

(3) A method using cesium carbonate as a base, thiophenol as a thiol, and N,N-dimethylformamide as a solvent (*J. Org. Chem.*, 62: 1586 (1997));

(4) A method using diisopropylethylamine as a base, thiophenol as a thiol, and N,N-dimethylformamide as a solvent (*Tetrahedron Lett.*, 39: 3889 (1998));

(5) A method using n-propylamine as a base, thiophenol as a thiol, and dimethoxyethane as a solvent (JP-A-11-171860);

(6) A method using lithium hydroxide as a base, thioglycolic acid as a thiol, and N,N-dimethylformamide as a solvent (*Tetrahedron Lett.*, 36: 6373 (1995)); and (7) A method using 1,8-diazabicyclo[5.4.0]-7-undecene as a base, mercaptoethanol as a thiol, and N,N-dimethylformamide as a solvent (*J. Am. Chem. Soc.*, 119: 2301 (1997)).

DISCLOSURE OF THE INVENTION

However, in any of the above methods, the ill-smelling thiol compounds have to be used. For industrially carrying out the above-described methods, there is the serious problem that special equipment in which consideration for the environment such as smell-removing measures is taken is required, or that treatment for making the thiol compounds odorless after reaction, which are ordinarily used in excess, becomes necessary. Accordingly, the development of a method for removing the 2- or 4-nitrobenzenesulfonyl group has been desired which can avoid the use of a thiol, is simple, has general-purpose properties, and is more industrially advantageous.

In view of the above-described state, the present inventor has made intensive studies for solving such a problem. As a result, the inventor has discovered that the nitrobenzenesulfonyl group bonded to an amino group can be easily removed to convert the nitrobenzenesulfonamide to a corresponding amine by allowing an alkali metal alkoxide to act on a 2- or 4-nitrobenzenesulfonamide, thus completing the present invention.

That is to say, the present invention relates to a method for removing a nitrobenzenesulfonyl group from a nitrobenzenesulfonamide and a method for producing an amine derivative using this method, having the following constitutions:

1. A method for removing a nitrobenzenesulfonyl group from a compound represented by the following formula (1), which comprising bringing the compound represented by formula (1) into contact with an alkali metal alkoxide:

wherein $R_1$ and $R_2$, which are the same or different, each represents a hydrogen atom or an aliphatic or alicyclic hydrocarbon group which may be substituted, or an atomic group in which $R_1$ and $R_2$ combine with each other at their ends together with an adjacent nitrogen atom to form a cyclic amine which may be substituted; and Ns represents a 2-nitrobenzenesulfonyl group or a 4-nitrobenzenesulfonyl group.

2. The method according to the above item 1, wherein the compound represented by formula (1) is a nitrobenzenesulfonamide of an α-amino acid derivative or a β-amino acid derivative.

3. The method according to the above item 1, wherein the compound represented by formula (1) is a nitrobenzenesulfonamide of an amino alcohol derivative.

4. The method according to any one of the above items 1 to 3, wherein the alkali metal alkoxide is an alkali metal methoxide.

5. The method according to any one of the above items 1 to 4, wherein the alkali metal in the alkali metal alkoxide is lithium or sodium.

6. A method for producing an amine derivative represented by the following formula (2), which comprises converting the compound represented by formula (1) to a compound in which the nitrobenzenesulfonyl group is removed according to the method according to any one of the above items 1 to 5, and allowing the compound without isolation to react with an activated substituted oxycarbonyl compound or an activated acyl compound:

wherein $R_1$ and $R_2$ are the same as described above, and $R_3$ represents a substituted oxycarbonyl group or an acyl group.

BEST MODE FOR CARRYING OUT THE INVENTION

The present invention is described in detail below.

First, the 2- or 4-nitrobenzenesulfonamide used as a starting material in the present invention is represented by the following formula (1):

wherein $R_1$ and $R_2$, which are the same or different, each represents a hydrogen atom or an aliphatic or alicyclic hydrocarbon group which may be substituted, or an atomic group in which $R_1$ and $R_2$ combine with each other at their ends together with an adjacent nitrogen atom to form a cyclic amine which may be substituted; and Ns represents a 2-nitrobenzenesulfonyl group or a 4-nitrobenzenesulfonyl group.

The above-described compound (hereinafter referred to as compound (1)) is usually synthesized by allowing a corresponding amine with a 2- or 4-nitrobenzenesulfonyl halide in a solvent, in the coexistence of a base. As the 2- or 4-nitrobenzenesulfonyl halide, a chloride thereof is suitably used.

Furthermore, as the above-described base, either an organic base or an inorganic base can be used. As the organic base, generally, a tertiary amine which does not consume the 2- or 4-nitrobenzenesulfonyl halide by reaction with the reagent is suitably used. Examples include trimethylamine, triethyl amine, tri-n-propyl amine, tri-n-butyl amine, disopropylethylamine, N,N,N',N'-tetramethylethylenediamine, N,N,N',N'-tetramethyl-1,3-propanediamine, N-methylmorpholine, N,N'-dimethylpiperazine, 1,4-diazabicyclo[2.2.2]octane, 1,5-diazabicyclo[4.3.0]-5-nonene, 1,8-diazabicyclo[5.4.0]-7-undecene and the like. Heterocyclic aromatic amines such as pyridine, 4-dimethylaminopyridine, collidine, lutidine and the like are also available.

Examples of the inorganic base include alkali metal hydroxides such as lithium hydroxide, sodium hydroxide, potassium hydroxide and the like, alkaline earth metal hydroxides such as magnesium hydroxide, calcium hydroxide, barium hydroxide and the like, alkaline metal carbonates such as lithium carbonate, sodium carbonate, potassium carbonate, cesium carbonate and the like, and quaternary ammonium hydroxides such as tetrabutylammonium hydroxide, tetraethylammonium hydroxide, tetramethylammonium hydroxide and the like.

Although there is no particular limitation on the solvent used in the reaction, suitably used are organic solvents, water, mixed solvents of hydrophilic organic solvents and water, and the like, which are usually often employed. Examples of these solvents include methylene chloride, chloroform, N,N-dimethylformamide, acetonitrile, dioxane, tetrahydrofuran, dimethoxyethane, tert-butyl alcohol, water-dioxane, water-tetrahydrofuran and the like.

Furthermore, besides synthesis by sulfonylation of the amine as described above, compound (1) can also be synthesized by further conversion of a compound already having the nitrobenzenesulfonyl group, and can also be synthesized through alkylation from an alkali metal salt of the nitrobenzenesulfonamide.

As an example of conversion of the compound already having the nitrobenzenesulfonyl group, for example, JP-A-11-171855 discloses an example of synthesis of (S)-N-(2-nitrobenzenesulfonyl)azetidine-2-carboxylic acid by cyclization of methyl (S)-N-(2-nitrobenzenesulfonyl)-α-amino-γ-iodobutyrate and subsequent hydrolysis. Furthermore, an example is described in *Tetrahedron Lett.*, 38: 5253 (1997) in which N-(4-nitrobenzenesulfonyl)-1-substituted-2-propylamine substituted by each of various nucleophiles is synthesized by ring opening reaction of 2-methylnosylaziridine (nosyl and nitrobenzenesulfonyl have the same meaning) with the nucleophiles. Still furthermore, an example is described in *J. Am. Chem. Soc.*, 122, 976 (2000) in which optically active [N-(4-trifluoromethylphenyl)phenylmethyl]-4-nitrobenzenesulfonamide is synthesized by introducing a phenyl group by nucleophilic addition into an N-alkylidenesulfonamide prepared from 4-trifluoromethylbenzaldehyde and 4-nitrobenzenesulfonamide.

Furthermore, as an example of synthesis through alkylation from the alkali metal salt of the nitrobenzenesulfonamide, a production example is describe, for example, in *Angew. Chem. Int. Ed.*, 39: 1323 (2000) in which optically active methyl β-substituted-β-N-(2-nitrobenzenesulfonyl)aminopropionate is produced by reaction of a sodium salt of 2-nitrobenzenesulfonamide with β-lactone variously substituted. Still furthermore, an example is described in *J. Am. Chem. Soc.*, 121:6761 (1999) in which an optically active N-(2-nitrobenzenesulfonyl) benzylallylamine derivative is produced by reaction of a lithium salt of N-(2-nitrobenzenesulfonyl)benzylamine with an allyl carbonate derivative.

$R_1$ and $R_2$ of compound (1), which are the same or different, each represents a hydrogen atom or an aliphatic or alicyclic hydrocarbon group which may be substituted, or an atomic group in which $R_1$ and $R_2$ combine with each other at their ends together with an adjacent nitrogen atom to form a cyclic amine which may be substituted.

The aliphatic or alicyclic hydrocarbon group of the aliphatic or alicyclic hydrocarbon group which may be substituted includes a straight-chain, branched or cyclic hydrocarbon group having from 1 to 10 carbon atoms, and specifically, it is methyl, ethyl, vinyl, ethynyl, n-propyl, isopropyl, cyclopropyl, allyl, propargyl, n-butyl, isobutyl, sec-butyl, tert-butyl, cyclobutyl, cyclopentyl, neopentyl, cyclohexyl, n-octyl or the like. These groups may be substituted at any positions at which they are substitutable. Although asymmetric carbon atoms can be produced by substitution, the asymmetric carbon atoms may be contained in the above-described groups. That is to say, they may be optically active.

Substituents by which the above-described hydrocarbon groups may be substituted include a hydroxyl group, a carboxylic acid group, an ester group, an amido group, an amino group, a cyano group, an alkoxyl group, an alkylthio group, an arylthio group, an aryl group, a heterocyclic group, a halogen atom and the like. Specifically, they include an ester group such as methoxycarbonyl, ethoxycarbonyl, isopropyloxycarbonyl, tert-butoxycarbonyl, benzyloxycarbonyl or the like, an amido group such as carbamoyl, N-methylcarbamoyl, N,N-dimethylcarbamoyl, N-ethylcarbamoyl, N,N-diethylcarbamoyl, N,N-dibenzylcarbamoyl or the like, an amino group such as amino, N-methylamino, N,N-dimethylamino, N-ethylamino, N,N-diethylamino, N-benzylamino, N,N-dibenzylamino or the like, an alkoxyl group such as methoxy, ethoxy, isopropoxy, tert-butoxy, benzyloxy or the like, an alkylthio group such as methylthio, ethylthio, benzylthio or the like, an arylthio group such as phenylthio or the like, an aryl group such as phenyl, tolyl, naphthyl or the like, a heterocyclic group such as azetidinyl, pyrrolidinyl, piperidyl, piperazinyl, morpholinyl, tetrahydrofuranyl, tetrahydropyranyl, furyl, thienyl, imidazolyl, pyridyl, quionlyl, isoquinolyl or the like, and a halogen atom such as fluorine, chlorine, bromine, iodine or the like.

Furthermore, when $R_1$ and $R_2$ combine with each other at their ends together with an adjacent nitrogen atom to form a cyclic amine which may be substituted, the cyclic amine includes, for example, an azetidine ring, a pyrrolidine ring, a piperidine ring and the like. These rings may be substituted at any positions at which they are substitutable. Similarly to the case of the above-described aliphatic or alicyclic hydrocarbon groups, asymmetric carbon atoms can be produced. However, the asymmetric carbon atoms may be contained in the above-described groups. That is to say, they may be optically active. Substituents by which the above-described rings may be substituted include substituents similar to those for the above-described aliphatic or alicyclic hydrocarbon groups.

Furthermore, substituent Ns in compound (1) is a 2-nitrobenzenesulfonyl group or a 4-nitrobenzenesulfonyl group.

Compound (1) useful as an intermediate of a pharmaceutical or an agricultural chemical includes a nitrobenzenesulfonamide of (S)-3-aminopyrrolidine, (S)-3-amino-2-pyrrolidone or the like, and the like, as well as a nitrobenzenesulfonamide of an α-amino acid derivative such as (S)-azetidine-2-carboxylic acid, (R)-proline or the like, a nitrobenzenesulfonamide of a β-amino acid derivative such as (S)-phenyl-β-alanine, (S)-3-pyridyl-β-alanine or the like, and a nitrobenzenesulfonamide of an amino alcohol derivative such as (R)-phenylglycinol, (1R,2R)-1-amino-2-indanol, (R)-1-(3-pyridyl)-2-aminoethanol, (R)-1-(3-chlorophenyl)-2-aminoethanol, (S)-3-hydroxypyrrolidine or the like.

Then, removing reaction of the nitrobenzenesulfonyl group by the contact of compound (1) with the alkali metal alkoxide is described.

The alkali metal alkoxides used in this removing reaction include lithium methoxide, sodium methoxide, potassium methoxide, lithium ethoxide, sodium ethoxide, sodium tert-butoxide, potassium tert-butoxide and the like. The alkoxide is preferably a methoxide, and the alkali metal is preferably sodium or lithium. Sodium methoxide is particularly preferred among others. As the above-described alkali metal alkoxides, either ones which can usually be purchased can be used as such, or for example, ones generated from organolithium compounds or alkali metal amide compounds and the corresponding alcohols in the reaction system can be used, if necessary.

As to the amount of the alkali metal alkoxide used, when compound (1) has no substituent reactive with the alkali metal alkoxide, the amount equimolar or more to compound (1) is required. However, from the economical point, the amount nearer to the equimolar amount is more desirable. On the other hand, when compound (1) has substituents reactive with the alkali metal alkoxide (for example, a carboxyl group or a hydroxyl group), it is necessary to use the alkali metal alkoxide in an amount of at least the number of moles obtained by adding 1 to the number of these substituents. Usually, it is suitably used in a 0.5- to 2.5-fold molar equivalent excess, in addition to the calculated amount.

The above-described reaction is usually conducted in a solvent. There is no particular limitation on the solvent used, as long as it does not inactivate the alkali metal alkoxide. Examples include aliphatic hydrocarbon solvents such as hexane, heptane and the like, aromatic hydrocarbon solvents such as toluene, xylene and the like, ether solvents such as tetrahydrofuran, dimethoxyethane, dioxane, tert-butyl methyl ether, isopropyl ether and the like, nitrile solvents such as acetonitrile, propionitrile and the like, amide solvents such as N,N-dimethylformamide and the like, sulfoxide solvents such as dimethyl sulfoxide and the like, alcohol solvents such as methanol, ethanol and the like, and the like. Ether solvents are particularly suitably used. These solvents may be used either alone or as a mixture of two or more of them. Although the amount thereof used is within the range of from the 5- to 40-fold solvent volume (ml) based on the substrate mass (g) of compound (1), the smaller amount is desirable, considering economy and productivity.

The reaction temperature is preferably 0° C. or higher, and more preferably 20° C. or higher from the viewpoint of reaction speed. The upper limit is the boiling point of the solvent. The reaction time is considerably different depending on the reaction conditions, so that it is difficult to show it generally. However, usually, a reaction solution is analyzed with time by use of analytical means of common use such as thin layer chromatography (TLC), high performance liquid chromatography (HPLC), gas chromatography (GLC) and the like, and the disappearance of starting materials is confirmed, thereby knowing the end point of the reaction. Thus, the reaction can be terminated.

The product in which the nitrobenzenesulfonyl group has been removed by the above-described reaction is isolated as described below, as needed.

When a water-soluble solvent is used as the reaction solvent, the reaction solvent is first removed by evaporation prior to extraction. However, it is not necessarily removed by evaporation in some cases. The reaction solvent may be removed by evaporation either after or before neutralization of the alkali metal alkoxide used with an acid, but preferably after neutralization. Alternatively, when the reaction solvent is not water-soluble, it may not be removed by evaporation, and neutralization and extraction are conducted as such.

Although there is no particular limitation on the acid used for neutralization of the alkali metal alkoxide used, an inorganic acid is usually employed. Preferably, hydrochloric acid, sulfuric acid or the like appropriately diluted is used. In the succeeding extraction, the product is an amine, so that the solution is made acidic to convert the amine to a salt with an acid, and the desired product is first extracted with acidic water into an aqueous layer, for separating the desired product from a by-product derived from the nitrobenzenesulfonyl group in the above-described reaction. Then, the aqueous layer is made basic, and the desired product is extracted as a free amine with a suitable solvent.

An alkali used for making the aqueous layer basic is an alkali metal hydroxide, an alkali metal carbonate or the like, and an aqueous solution of sodium hydroxide, an aqueous solution of sodium carbonate or the like is suitably used. Although there is no particular limitation on the solvent used for extraction, ether, hexane, ethyl acetate, toluene or the like can be suitably used. When the reaction product is a highly water soluble compound such as a free amino acid or the like, water extraction is conducted with acidic water in the same manner as described above, followed by adjustment to a suitable pH, and isolation and purification can also be conducted using an ion exchange resin.

Usually, the desired product isolated as described above has a purity sufficient to carry out further conversion. However, the purity may be further heightened by chromatography, crystallization, distillation or the like if necessary.

Furthermore, the product in which the nitrobenzenesulfonyl group is removed in the above-described reaction is not necessarily required to be isolated, and a substituted oxycarbonyl group or an acyl group can be introduced into a free amino group to produce a compound represented by formula (2) (hereinafter referred to as compound (2)).

Then, the method of the present invention for producing compound (2) is described.

Substituents $R_1$ and $R_2$ in compound (2) are the same as in compound (1). Furthermore, substituent $R_3$ is a substituted oxycarbonyl group or an acyl group. The substituted oxycarbonyl group as used herein indicates an alkoxycarbonyl group usually often used as a protective group, and includes, for example, methoxycarbonyl, ethoxycarbonyl, tert-butoxycarbonyl, allyloxycarbonyl, benzyloxycarbonyl and the like. The acyl group includes, for example, formyl, acetyl, chloroacetyl, trifluoroacetyl, trichloroacetyl, benzoyl and the like, which are usually often used as a protective group. Besides, the acyl group may be an acyl residue of an amino acid appropriately protected.

For introducing the above-described substituent $R_3$ into the compound in which the nitrobenzenesulfonyl group is removed from compound (1) to convert it to compound (2), a base may be allowed to coexist newly after neutralization of the solution subjected to the above-described removing reaction, and to react with an activated, substituted oxycarbonyl compound or an activated acyl compound. The activated, substituted oxycarbonyl compound as used herein is, for example, a substituted oxycarbonyl compound activated in the form of a halide, an active ester, an anhydride, an azide, a cyanide or the like, and includes, for example, methyl chlorocarbonate, ethyl chlorocarbonate, di-tert-butyl dicarbonate, tert-butoxycarbonylazide, diallyl dicarbonate, benzyl chlorocarbonate, dibenzyl dicarbonate and the like. Furthermore, the activated acyl compound is an acyl compound activated in the form of a halide, an active ester, an anhydride, an active amide, a cyanide or the like, and includes, for example, acetic anhydride, acetyl chloride, pentafluorophenyl acetate, p-nitrophenyl acetate, acetylimidazole, trifluoroacetic acid anhydride, benzoyl chloride, benzoyl cyanide and the like. In either case of the activated, substituted oxycarbonyl compound and the activated acyl compound, usually, a chloride is suitably used.

Although there is no particular limitation on the base allowed to coexist in the reaction, there can be used, for example, an organic tertiary amine such as triethylamine, diisopropylethylamine, pyridine or the like, an inorganic base such as sodium carbonate, potassium carbonate, sodium hydrogen carbonate, sodium hydroxide, magnesium oxide or the like, or the like. As a solvent for the above-described reaction, the solvent used in the preceding reaction may be either used as such, or replaced by another solvent as needed.

Compound (2) produced as described above is isolated by extraction and concentration after removal of the reaction solvent by evaporation if necessary. In extraction, for example, toluene, ethyl acetate or the like is suitably used. The product isolated by concentration may be further heightened in the purity by chromatography, crystallization, distillation or the like as needed.

EXAMPLES

The present invention is described with reference to examples in greater detail, but it would be understood that the present invention is not limited thereto.

Reference Example 1

Preparation of N-(2-nitrobenzenesulfonyl) benzhydrylamine

N-(2-Nitrobenzenesulfonyl)benzhydrylamine used in the following examples was prepared as described below.

2-Nitrobenzenesulfonyl chloride (2.50 g) was added to a methylene chloride solution (30 ml) containing benzhydrylamine (1.87 g) and triethylamine (1.58 g) under ice cooling, followed by stirring for 3.3 hours under ice cooling and for 68.7 hours at room temperature. Water (40 ml), 6 N hydrochloric acid (2 ml) and methylene chloride (10 ml) were added to the reaction mixture, followed by extraction and solution separation, and the aqueous layer was extracted again with methylene chloride (10 ml). The resulting extract was dried over sodium sulfate, filtered, concentrated and further dissolved again in ethyl acetate (70 ml), followed by washing with water (20 ml). The organic layer was dried over sodium sulfate, filtered, concentrated and dried under vacuum to obtain N-(2-nitrobenzenesulfonyl) benzhydrylamine (3.71 g; yield: 98.7%).

Reference Example 2

Preparation of N-(4-nitrobenzenesulfonyl) benzhydrylamine

N-(4-Nitrobenzenesulfonyl)benzhydrylamine used in the following examples was prepared as described below.

4-Nitrobenzenesulfonyl chloride (2.51 g) was added to a methylene chloride solution (30 ml) containing benzhydrylamine (2.12 g) and triethylamine (1.62 g) under ice cooling, followed by stirring for 3 hours under ice cooling and for 69 hours at room temperature. Water (30 ml), 1 N hydrochloric acid (12 ml) and methylene chloride (5 ml) were added to the reaction mixture, followed by extraction and solution separation, and the aqueous layer was extracted again with methylene chloride (10 ml). The resulting extract was concentrated, and ethyl acetate (80 ml) and water (50 ml) were further added, followed by solution separation. The organic layer was washed in turn with saturated aqueous solution of sodium bicarbonate (10 ml) and water (25 ml), and concentrated. The resulting solid was washed with a mixed solution of ether (9 ml)/hexane (20 ml) and successively with hexane (10 ml), and dried under vacuum to obtain N-(4-nitrobenzenesulfonyl)benzhydrylamine (3.81 g; yield: 91.3%).

Reference Example 3

Preparation of (S)-N-(2-nitrobenzenesulfonyl) proline (S)-N-(2-Nitrobenzenesulfonyl)proline used in the following example was prepared as described below.

2-Nitrobenzenesulfonyl chloride (5.79 g) was added to a mixed solution of tetrahydrofuran (20 ml)/water (17 ml) containing (S)-proline (2.00 g), 5 N sodium hydroxide (3.5 ml) and sodium carbonate (3.77 g) under ice cooling, followed by stirring for 1 hour under ice cooling and for 22 hours at room temperature. Water (20 ml) was added to the reaction mixture, and the organic solvent was removed by evaporation under reduced pressure. Then, water (20 ml), 5 N sodium hydroxide (4 ml) and ethyl acetate (100 ml) were added, followed by extraction and solution separation, and the organic layer was extracted again with water (15 ml). Ethyl acetate (50 ml) and 6 N hydrochloric acid (20 ml) were added to the resulting aqueous layer, followed by extraction and solution separation, and the aqueous layer was extracted again with ethyl acetate (50 ml). The resulting organic layer was dried over sodium sulfate, filtered, concentrated and dried under vacuum to obtain (S)-N-(2-nitrobenzenesulfonyl)proline (5.53 g; yield: quantitative).

Reference Example 4

Preparation of (S)-N-(2-nitrobenzenesulfonyl) azetidine-2-carboxylic acid (S)-N-(2-Nitrobenzenesulfonyl)azetidine-2-carboxylic acid used in the following examples was prepared as described below.

A mixed solution of tetrahydrofuran (70 ml)/water (60 ml) containing (S)-N-(tert-butoxycarbonyl)azetidine-2-carboxylic acid (20.51 g; also containing (R)-isomer) and sulfuric acid (10.03 g) was stirred for 1 hour under ice cooling, 1.5 hours at room temperature, and for 28 hours under heating at 45 to 48° C. On the way, 6 N hydrochloric acid (20 ml) was further added after about 20 hours. The reaction mixture was cooled with ice, and sodium carbonate (38.92 g), 2-nitrobenzenesulfonyl chloride (29.42 g), tetrahydrofuran (50 ml) and water (60 ml) were added in turn thereto, followed by stirring for 70 minutes under ice cooling and for 37 hours at room temperature. On the way, sodium carbonate (5.45 g) was further added after 30 minutes. Water (140 ml) was added to the reaction mixture, and the organic solvent was removed by evaporation under reduced pressure. Then, water (40 ml) and ethyl acetate (140 ml) were added, followed by extraction and solution separation, and the organic layer was extracted again with water (100 ml). Ethyl acetate (30 ml) and concentrated hydrochloric acid (40 ml) were added to the resulting aqueous layer, and ethyl acetate (100 ml) was further added, followed by extraction and solution separation. The aqueous layer was extracted again with ethyl acetate (120 ml). The resulting organic layer was dried over sodium sulfate, filtered, concentrated and dried under vacuum to obtain (S)-N-(2-nitrobenzenesulfonyl)azetidine-2-carboxylic acid (26.2 g; yield: 89.8%). Analysis according to high performance liquid chromatography (HPLC) resulted in 46.4% ee. Conditions of HPLC analysis:

Column: Chiralcel OD-R (manufactured by Daicel Chemical Industries, Ltd.)

Mobile phase: Acetonitrile/aqueous solution of perchloric acid (pH 2.0)=99/1 (Vol/Vol)

Detection: 210 nm

Reference Example 5

Preparation of (S)-2-[N-(2-nitrobenzenesulfonyl)amino]-6-(N-benzylamino)-6-methyl-4-heptynoic acid (S)-2-[N-(2-nitrobenzenesulfonyl)amino]-6-(N-benzylamino)-6-methyl-4-heptynoic acid used in the following example was prepared by the same method as described in Japanese Patent Application No. Hei 12-039415 using (S)-N-(2-nitrobenzenesulfonyl)aziridine-2-carboxylic acid, N-benzyl-1,1-dimethylpropargylamine and n-butyllithium.

Reference Example 6

Preparation of (R)-N-(2-nitrobenzenesulfonyl)phenylglycinol (R)-N-(2-Nitrobenzenesulfonyl)phenylglycinol used in the following example was prepared as described below.

A tetrahydrofuran solution (10 ml) containing 2-nitrobenzenesulfonyl chloride (3.28 g) was added to a mixed solution of tetrahydrofuran (20 ml)/water (5 ml) containing (R)-phenylglycinol (1.85 g) and triethylamine (2.11 g) at room temperature, followed by stirring for 70.5 hours. The organic solvent was removed from the reaction mixture by evaporation under reduced pressure. Then, water (20 ml) and ethyl acetate (30 ml) were added, followed by extraction and solution separation, and the aqueous layer was extracted again with ethyl acetate (15 ml). The resulting extract was filtered through a short column filled with silica gel (30.17 g), and the silica gel was washed with ethyl acetate to confirm the termination of elution of the desired product. The resulting filtrate was concentrated and dried under vacuum to obtain (R)-N-(2-nitrobenzenesulfonyl)phenylglycinol (4.08 g; yield: 93.8%).

Example 1

Removal of Nitrobenzenesulfonyl Group and Synthesis of Benzhydrylamine

A 28% sodium methoxide/methanol solution (0.34 ml; 1.52 molar equivalents) was added to a solution of N-(2-nitrobenzenesulfonyl)benzhydrylamine (401.6 mg) in dry dioxane (3 ml) at room temperature in an argon atmosphere, followed by stirring for 23 hours at room temperature. The reaction solvents were removed by evaporation under reduced pressure, and water (10 ml), 2 N sulfuric acid (1.5 ml) and ether (15 ml) were added to the resulting concentrate, followed by extraction and solution separation. The organic layer was extracted again with water (5 ml). To the resulting aqueous layer, 5 N sodium hydroxide (1 ml) was added, and extraction was conducted twice with ether (13 ml), followed by drying over sodium sulfate, filtration, concentration and drying under vacuum to obtain benzhydrylamine (205.2 mg; yield: quantitative).

$^1$H-NMR (CDCl$_3$) δ1.79 (br s, 2H), 5.21 (s, 1H), 7.18–7.42 (m, 10H)

Example 2

Removal of Nitrobenzenesulfonyl Group and Synthesis of Benzhydrylamine

A 28% sodium methoxide/methanol solution (0.42 ml; 1.49 molar equivalents) was added to a solution of N-(2-nitrobenzenesulfonyl)benzhydrylamine (503.3 mg) in dry tetrahydrofuran (5 ml) at room temperature in an argon atmosphere, followed by stirring for 2 hours at room temperature. When water (8.5 ml), 3 N hydrochloric acid (1.5 ml) and ether (5 ml) were added to the concentrate obtained by removing the reaction solvents by evaporation under reduced pressure, an insoluble solid was observed. Accordingly, 2 N sulfuric acid (1.5 ml) and ether (10 ml) were further added. The insoluble solid remained, so that it was separated by filtration. Solution separation was conducted for the filtrate, and the organic layer was extracted again with a mixed solution of 2 N sulfuric acid (1 ml)/water (9 ml). Five normal sodium hydroxide (4 ml) was added to the resulting aqueous layer, which was combined with the solid previously separated by filtration, and extraction was conducted four times with ether (10 ml), followed by drying over sodium sulfate, filtration and concentration. Hexane (15 ml) was added to the concentrate containing the solid, and insoluble matter was filtered and washed with hexane (10 ml). The resulting filtrate was concentrated and dried under vacuum to obtain benzhydrylamine (164.3 mg; yield: 65.6%). Furthermore, the ether layer remained in the preceding extraction with water was dried over sodium sulfate and filtered, and combined with the filtered solid obtained after above-described washing with hexane, followed by concentration. Hexane (15 ml) was added to the concentrate containing the solid, and the solid was filtered and washed with hexane (10 ml), followed by drying under vacuum to recover unreacted materials (162.3 mg; yield: 32.2%).

Example 3

Removal of Nitrobenzenesulfonyl Group and Synthesis of Benzhydrylamine

A 28% sodium methoxide/methanol solution (0.34 ml; 1.51 molar equivalents) was added to a solution of N-(2- nitrobenzenesulfonyl)benzhydrylamine (402.1 mg) in dry acetonitrile (3 ml) at room temperature in a nitrogen atmosphere, followed by stirring for 27 hours at room temperature. On the way, a 28% sodium methoxide/methanol solution (0.34 ml; 1.51 molar equivalents) was further added after 10 hours. The reaction mixture was cooled with ice, 1 N hydrochloric acid (5 ml) was added, and the reaction solvents were removed by evaporation under reduced pressure. Water (5 ml), 1 N hydrochloric acid (5 ml) and ether (30 ml) were added to the resulting concentrate, followed by extraction and solution separation, and the organic layer was extracted again with water (5 ml). Sodium hydroxide (0.62 g) was added to the resulting aqueous layer, and extraction was conducted three times with ether (20 ml), followed by drying over sodium sulfate, filtration, concentration and drying under vacuum to obtain benzhydrylamine (155.9 mg; yield: 77.9%).

Example 4

Removal of Nitrobenzenesulfonyl Group and Synthesis of Benzhydrylamine

A 28% sodium methoxide/methanol solution (0.34 ml; 1.51 molar equivalents) was added to a solution of N-(2-nitrobenzenesulfonyl)benzhydrylamine (402.1 mg) in dimethyl sulfoxide (2 ml) at room temperature in a nitrogen atmosphere, followed by stirring for 95 hours at room temperature. On the way, a 28% sodium methoxide/methanol solution (0.34 ml; 1.51 molar equivalents) was further added after 22.5 hours. To the reaction mixture, 1 N hydrochloric acid (6 ml), water (5 ml) and ether (20 ml) were added, followed by extraction and solution separation. The organic layer was extracted again with water (3 ml). Sodium hydroxide (0.32 g) was added to the resulting aqueous layer, and extraction was conducted twice with ether (20 ml). After the organic layer was washed with water (6 ml), it was dried over sodium sulfate, filtered, concentrated and dried under vacuum to obtain 135.6 mg of an oily product. This product obtained contained ingredients other than the desired product, so that the following treatment was conducted. Hexane (20 ml), 1 N hydrochloric acid (3 ml) and water (4 ml) were added to the above-described oily product, followed by solution separation, and the organic layer was extracted again with water (5 ml). Sodium hydroxide (0.47 g) was added to the resulting aqueous layer, and extraction was conducted with hexane (30 ml). The organic layer was dried over sodium sulfate, filtered, concentrated and dried under vacuum to obtain 116.8 mg of an oily product. This oily product was similarly treated again to obtain a benzhydrylamine-containing oily product (96.4 mg; yield: less than 48%).

Example 5

Removal of Nitrobenzenesulfonyl Group and Synthesis of Benzhydrylamine

A 28% sodium methoxide/methanol solution (0.34 ml; 1.51 molar equivalents) was added to a solution of N-(4-nitrobenzenesulfonyl)benzhydrylamine (402.0 mg) in dry dimethoxyethane (3 ml) at room temperature in a nitrogen atmosphere, followed by stirring for 7 hours at room temperature and for 40 hours under heating at 46 to 49° C. On the way, dry dimethoxyethane (3 ml) was further added after 7 hours, and a 28% sodium methoxide/methanol solution (0.34 ml; 1.51 molar equivalents) was further added about 18 hours after heating. The reaction mixture was cooled with ice, and 1 N hydrochloric acid (5 ml) was added. The reaction solvents were removed by evaporation under reduced pressure, and water (5 ml), 1 N hydrochloric acid (5 ml) and ether (25 ml) were added to the resulting concentrate, followed by extraction and solution separation. The organic layer was extracted again with water (5 ml). Sodium hydroxide (0.61 g) was added to the resulting aqueous layer, and extraction was conducted three times with ether (20 ml), followed by drying over sodium sulfate, filtration, concentration and drying under vacuum to obtain benzhydrylamine (191.2 mg; yield: 95.6%).

Example 6

Removal of Nitrobenzenesulfonyl Group and Synthesis of (S)-N-benzyloxycarbonylproline A 28% sodium methoxide/methanol solution (1.65 ml; 2.50 molar equivalents) was added to a solution of (S)-N-(2-nitrobenzenesulfonyl)proline (963.5 mg) in dry N,N-dimethylformamide (10 ml) at room temperature in a nitrogen atmosphere, followed by stirring for 4 hours at room temperature. The reaction mixture was cooled with ice. Then, 1 N hydrochloric acid (8 ml), successively triethylamine (1.8 ml; 4.0 molar equivalents) and benzyloxycarbonyl chloride (0.78 ml; 1.7 molar equivalents) were added, followed by stirring for 1 hour under ice cooling and for 65 hours at room temperature. The reaction solvents were removed by evaporation under reduced pressure, and water (40 ml), 5 N sodium hydroxide (0.7 ml) and ether (30 ml) were added to the resulting concentrate, followed by extraction and solution separation. The organic layer was extracted again with water (5 ml). One normal hydrochloric acid (7 ml) was added to the resulting aqueous layer, and extraction was conducted three times with ether (30 ml), followed by drying over sodium sulfate, filtration, concentration and drying under vacuum to obtain 666.3 mg of an oily product. This oily product was purified by silica gel column chromatography (developing solution: methylene chloride/hexane=1/1 to 2/1→ethyl acetate/hexane=1/5 to 3/10) to obtain (S)-N-benzyloxycarbonylproline (364.2 mg; overall yield: 45.5%). HPLC analysis conducted under the same conditions as in Reference Example 4 resulted in 100% ee.

$^1$H-NMR (CDCl$_3$) δ1.96 (m, 2H), 2.05–2.35 (m, 2H), 3.49 (m, 2H), 4.42 (m, 1H), 5.18 (m, 2H), 7.34 (m, 5H)

Example 7

Removal of Nitrobenzenesulfonyl Group and Synthesis of (S)-N-(tert-butoxycarbonyl)azetidine-2-carboxylic Acid A 28% sodium methoxide/methanol solution (0.77 ml; 2.50 molar equivalents) was added to a solution of (S)-N-(2-nitrobenzenesulfonyl)azetidine-2-carboxylic acid (429.4 mg; 46.4% ee) in dry dimethoxyethane (5 ml) at room temperature in a nitrogen atmosphere, followed by stirring for 3 hours at room temperature. One normal hydrochloric acid (2.25 ml), successively triethylamine (0.33 ml; 1.58 molar equivalents) and a dimethoxyethane solution (1.5 ml) containing di-tert-butyl dicarbonate (387.6 mg; 1.17 molar equivalents) were added to the reaction mixture, followed by stirring for 17 hours at room temperature. The reaction solvents were removed by evaporation under reduced pressure, and water (3 ml), ethyl acetate (15 ml) and 1 N hydrochloric acid (4 ml) were added to the resulting concentrate under ice cooling, followed by extraction and solution separation. The aqueous layer was extracted twice with ethyl acetate (15 ml and 10 ml). The resulting (developing solution: methylene chloride/hexane=1/1 to 2/1→ethyl acetate/hexane=1/10 to 1/2) to obtain (S)-N-(tert-butoxycarbonyl)azetidine-2-carboxylic acid (184.6 mg; overall yield: 61.1%). HPLC analysis conducted under the same conditions as in Reference Example 4 resulted in 38.8% ee.

$^1$H-NMR (CDCl$_3$) δ1.48 (s, 9H), 2.40–2.60 (br s, 2H), 3.80–4.00 (br s, 2H), 4.80 (t, 1H)

Example 8

Removal of Nitrobenzenesulfonyl Group and Synthesis of (S)-N-(tert-butoxycarbonyl)azetidine-2-carboxylic Acid A 1 M lithium methoxide/methanol solution (3.75 ml; 2.50 molar equivalents) was added to a solution of (S)-N-(2-nitrobenzenesulfonyl)azetidine-2-carboxylic acid (429.4 mg; 46.4% ee) in dry dimethoxyethane (5 ml) at room temperature in a nitrogen atmosphere, followed by stirring for 94 hours at room temperature. One normal hydrochloric acid (2.25 ml), successively triethylamine (0.33 ml; 1.58 molar equivalents) and a dimethoxyethane solution (1.5 ml) containing di-tert-butyl dicarbonate (397.7 mg; 1.20 molar equivalents) were added to the reaction mixture, followed by stirring for 24 hours at room temperature. On the way, water (6 ml) was further added for decreasing insoluble matter. The reaction solvents were removed by evaporation under reduced pressure, and ethyl acetate (15 ml) and 1 N hydrochloric acid (8 ml) were added to the resulting concentrate under ice cooling, followed by extraction and solution separation. The aqueous layer was extracted three times with ethyl acetate (15 ml). The resulting organic layer was dried over sodium sulfate, filtered and concentrated to obtain an oily product. This oily product was purified by silica gel column chromatography in the same manner as in Example 7 to obtain (S)-N-(tert-butoxycarbonyl)azetidine-2-carboxylic acid (146.5 mg; overall yield: 48.5%). HPLC analysis conducted under the same conditions as in Reference Example 4 resulted in 38.0% ee.

Example 9

Removal of Nitrobenzenesulfonyl Group and Synthesis of (S)-2-[N-(tert-Butoxycarbonyl)amino]-6-(N-benzylamino)-6-methyl-4-heptynoic Acid A 28% sodium methoxide/methanol solution (0.75 ml; 3.50 molar equivalents) was added to a solution of (S)-2-[N-(2-nitrobenzenesulfonyl)amino]-6-(N-benzylamino)-6-methyl-4-heptynoic acid (471.1 mg) in dry dimethoxyethane (7 ml) at room temperature in an argon atmosphere, followed by stirring for 43 hours at room temperature, and the disappearance of the starting materials was confirmed. Sulfuric acid (0.18 g) was added to the reaction mixture at room temperature, and stirred for 10 minutes, followed by concentration and evaporation to dryness to obtain a foamy product (0.78 g). Ethyl acetate (20 ml) and ethanol (4 ml) were added, and the mixture was heated with a dryer. Then, the insoluble matter was separated by filtration, and washed with ethyl acetate (3 ml). The solid separated by filtration was washed with methanol (9 ml), and the soluble matter was collected. Furthermore, the ethyl acetate/ethanol filtrate was concentrated, and ethyl acetate (10 ml) and water (3 ml) were added, followed by solution separation. The organic layer was extracted again with water (2 ml), and the resulting aqueous layer and the above-described methanol soluble matter were combined, followed by concentration and evaporation to dryness to obtain a foamy product (0.54 g). This was converted to (S)-2-[N-(2-tert-butoxycarbonyl)amino]-6-(N-benzylamino)-6-methyl-4-heptynoic acid, and the optical purity was analyzed. Thionyl chloride (0.6 ml) was slowly added dropwise to a solution of the above-described foamy product (0.54 g) in methanol (13 ml) under ice cooling, and the mixture was stirred overnight between a temperature under ice cooling and at room temperature. Thionyl chloride (0.6 ml) and methanol (3 ml) were further added under ice cooling, and the mixture was further stirred for 1.5 hours between a temperature under ice cooling and at room temperature, and for 5 hours under heating at 50° C. The reaction mixture was concentrated under reduced pressure, and ethyl acetate (10 ml) and a cold saturated aqueous solution of sodium bicarbonate (5 ml) were added to the concentrate, followed by solution separation. The aqueous layer was extracted again with ethyl acetate (12 ml). The resulting extracted layer was concentrated to about 5 ml, and an ethyl acetate solution (3 ml) containing di-tert-butyl dicarbonate (0.3 g) was added, followed by stirring for 1.5 hours at room temperature. Citric acid (0.75 g) and cold water (15 ml) were added to the reaction solution, followed by solution separation, and the organic layer was extracted again with cold water (8 ml). The desired product still remained in the organic layer, so that reextraction was further conducted with cold water (10 ml) containing citric acid (0.42 g). Sodium carbonate (1.45 g) was added to the resulting aqueous layer, which was extracted twice with ethyl acetate (25 ml and 22 ml), followed by drying over sodium sulfate, filtration, concentration and drying under vacuum to obtain (S)-2-[N-(tert-butoxycarbonyl)amino]-6-(N-benzylamino)-6-methyl-4-heptynoic acid (270 mg; overall yield: 68%). HPLC analysis was conducted under the following conditions. Analysis according to high performance liquid chromatography using an optically active column resulted in 96% ee.

Conditions of HPLC analysis:

Column: Chiralcel OD-H (manufactured by Daicel Chemical Industries, Ltd.)

Mobile phase: Hexane/2-propanol=99/1 (Vol/Vol)

Detection: 210 nm $^1$H-NMR (CDCl$_3$) δ1.37 (s, 6H), 1.45 (s, 9H), 2.68–2.86 (m, 2H), 3.76 (s, 3H), 3.82 (s, 2H), 4.48 (m, 1H), 5.32 (br d, 1H), 7.21–7.40 (m, 5H)

Example 10

Removal of Nitrobenzenesulfonyl Group and Synthesis of (R)-phenylglycinol

A 28% sodium methoxide/methanol solution (3.4 ml; 3.50 molar equivalents) was added to a solution of (R)-N-(2-nitrobenzenesulfonyl)phenylglycinol (1519.8 mg) in dry dimethoxyethane (15 ml) at room temperature in a nitrogen atmosphere, followed by stirring for 1 hour at room temperature, and for 2.5 hours under heating at 49 to 50° C. The reaction mixture was concentrated under reduced pressure, and water (10 ml), ether (30 ml) and an aqueous solution (5 ml) containing sulfuric acid (1.64 g) were added, followed by extraction and solution separation. The organic layer was extracted again with water (10 ml). Sodium hydroxide (2.18 g) was added to the resulting aqueous layer under ice cooling, and sodium sulfate was further added to saturation. Extraction was conducted three times with tetrahydrofuran (15 ml). The resulting extracted layer was concentrated, and dried under vacuum to obtain a solid-containing oily product. Tetrahydrofuran (20 ml) was added to this oily product, and insoluble matter was separated by filtration through a short column filled with sodium sulfate, followed by washing with tetrahydrofuran (5 ml). The resulting filtrate was concentrated and dried under vacuum to obtain 554 mg of an oily product. Water (7 ml) and activated carbon (20.7 mg) were added to this oily product, and heating by a dryer was carried out for 5 minutes. After standing to cool at room temperature, insoluble matter was separated by filtration through a short column of celite, and washed three times with water (1 ml). A filtrate aqueous solution was concentrated and evaporated to dryness to obtain (R)-phenylglycinol (416 mg; yield: 64.3%). HPLC analysis conducted under the following conditions resulted in 86.4% ee.

Conditions of HPLC analysis:
　Column: Crown Pack CR (+) (manufactured by Daicel Chemical Industries, Ltd.)
　Mobile phase: Methanol/aqueous solution of perchloric acid (pH 2.0)=99/1 (Vol/Vol)
　Detection: 210 nm
$^1$H-NMR (CDCl$_3$) δ3.52 (m, 1H), 3.68 (m, 1H), 4.00 (dd, J=4.4, 8.3 Hz, 1H), 7.22–7.33 (m, 5H)

Industrial Applicability

According to the method of the present invention, the 2- or 4-nitrobenzenesulfonamides are allowed to react with the alkali metal alkoxides, whereby the corresponding amines can be produced without using the thiol compounds, which are compounds having a strong bad smell.

Furthermore, substituted oxycarbonylation or acylation is possible without isolating the amines.

Thus, according to the method of the present invention, the amines or the amine derivatives can be produced easily and industrially advantageously by denitrobenzenesulfonylation.

What is claimed is:
1. A method for removing a nitrobenzenesulfonyl group from a compound represented by the following formula (1), which comprises bringing the compound represented by formula (1) into contact with an alkali metal alkoxide:

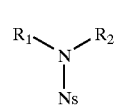

(1)

wherein $R_1$ and $R_2$, which are the same or different, each represents a hydrogen atom or an aliphatic or alicyclic hydrocarbon group which may be substituted, or an atomic group in which $R_1$ and $R_2$ combine with each other at their ends together with an adjacent nitrogen atom to form a cyclic amine which may be substituted; and Ns represents a 2-nitrobenzenesulfonyl group or a 4-nitrobenzenesulfonyl group.

2. The method according to claim 1, wherein the compound represented by formula (1) is a nitrobenzenesulfonamide of an α-amino acid derivative or a β-amino acid derivative.

3. The method according to claim 1, wherein the compound represented by formula (1) is a nitrobenzenesulfonamide of an amino alcohol derivative.

4. The method according to any one of claims 1 to 3, wherein the alkali metal alkoxide is an alkali metal methoxide.

5. The method according to any one of claims 1 to 3, wherein the alkali metal in the alkali metal alkoxide is lithium or sodium.

6. A method for producing an amine derivative represented by the following formula (2), which comprises converting the compound represented by formula (1) to a compound in which the nitrobenzenesulfonyl group is removed according to the method according to any one of claims 1 to 3, and allowing the compound without isolation to react with an activated substituted oxycarbonyl compound or an activated acyl compound:

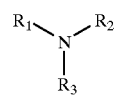

(2)

wherein $R_1$ and $R_2$ are the same as described above, and $R_3$ represents a substituted oxycarbonyl group or an acyl group.

* * * * *